(12) United States Patent
Buratowski et al.

(10) Patent No.: US 6,300,067 B1
(45) Date of Patent: Oct. 9, 2001

(54) **TFIIB TRANSCRIPTION FACTOR FROM *CANDIDA ALBICANS* AND METHODS OF SCREENING FOR INHIBITORS OF *CANDIDA ALBICANS* GROWTH**

(75) Inventors: Stephen Buratowski, Needham; C. Richard Wobbe, Lexington, both of MA (US); John Douglas Bradley, St. Louis, MO (US)

(73) Assignees: Scriptgen Pharmaceuticals, Medford; Harvard College, President & Fellows, Cambridge, both of MA (US)

( * ) Notice: Subject to any disclaimer, the term of this patent is extended or adjusted under 35 U.S.C. 154(b) by 0 days.

(21) Appl. No.: 09/204,841

(22) Filed: Dec. 3, 1998

Related U.S. Application Data

(62) Division of application No. 08/625,377, filed on Apr. 1, 1996, now Pat. No. 5,863,762.

(51) Int. Cl.⁷ .......................... C12Q 1/68; G01N 33/53; C07K 7/00; C07K 14/40
(52) U.S. Cl. ................. 435/6; 435/7.8; 530/300; 530/350
(58) Field of Search .................... 530/350, 300; 435/6, 7.8

(56) References Cited

U.S. PATENT DOCUMENTS 5,403,484  4/1995  Ladner et al. .

OTHER PUBLICATIONS

Colbert et al., *Genes & Development*, 6:1940–1949, 1992.
Fikes et al., *Nature*, 346:291–294, Jul. 19, 1990.
Hahn et al., *Cell*, 58:1173–1181, Sep. 22, 1989.
Horikoshi et al., *Nature*, 341:299–303, Sep. 28, 1989.
Killeen et al., *Journal of Biological Chemisty*, 267:9463–9466, May 15, 1992.
Khoo et al., *Genes & Development*, 8:2879–2890, 1994.
Lopez–De–Leon et al., *Cell*, 71:211–220, Oct. 16, 1992.
Moncollin et al., Proceedings of the National Acadamy of Sciences USA, 89:397–401, Jan. 1992.
Na et al., *Nucleic Acids Research*, 15:3413–3417, 1993.
Pinto et al., *Cell*, 68:977–988, Mar. 6, 1992.
Pinto et al., *Journal of Biological Chemistry*, 269:30569–30573, 1994.
Schmidt et al., Proceedings of the National Acadamy of Sciences USA, 86:7785–7789, Oct. 1989.
Buratowski et al., *Cell* 56:549–561, 1982.
Buratowski et al., *Proc. Natl. Acad. Sci. USA* 90:5633, 1993.
Edwards et al, *Proc. Natl. Acad. Sci. USA* 87:2122–2126, 1990.
Flores et al., *J. Biol. Chem.* 265(10):5629–5634, 1990.
Ha et al., *Nature* 352(22):689–695, 1991.
Hoffmann et al., *Nature* 346:387–390, 1990.
Jonsson et al., *Bio Techniques* 11(5):620–627, 1991.
Kao et al., *Science* 248:1646–1650, 1990.
Li et al., *Science* 263:805–807, 1994.
Lue et al., *Science* 246:661–664, 1989.
Parvin and Sharp, *Cell* 73:353–540, 1993.
Peterson et al., *Science* 248:1625–1630, 1990.
Reinberg and Roeder, *J. Biol. Chem.* 262(7):3310–3321, 1987.
Santos and Tuite, *Nuc. Acids. Res.* 23(9):1481–1486, 1995.
Sawdago and Roeder, *Proc. Natl. Acad. Sci. USA* 82:4394–4398, 1995.
Sayre et al., *J. Biol. Chem.* 267(32):23383–23387, 1992.
Slutsky et al., *Science* 230:666–669, 1985.

*Primary Examiner*—Terry McKelvey
(74) *Attorney, Agent, or Firm*—Darby & Darby

(57) ABSTRACT

The invention encompasses a novel transcription factor from *Candida albicans*, TFIIB, a nucleic acid sequence encoding TFIIB, and methods of screening for inhibitors of *Candida albicans* growth by targeting TFIIB.

9 Claims, 4 Drawing Sheets

FIG. IA

```
  1 ATG GAT TTA AAA TTA CCC CCA ACT AAT CCA ACC AAC CAA CAA GCA AAG ACT TTT ATG   60
  1  M   D   L   K   L   P   P   T   N   P   T   N   Q   Q   A   K   T   F   M    20

61 AAG TCA ATA GAG GAA GAT GAA AAA AAT AAA GCC GAA GAT TTG GAT ATT ATA AAG GAA  120
 21  K   S   I   E   E   D   E   K   N   K   A   E   D   L   D   I   I   K   E    40

121 GAC ATT GAT GAA CCT AAA CAA GAA GAT ACC GAT AGT AAT GGT GGA GGT ATT GGT      180
 41  D   I   D   E   P   K   Q   E   D   T   D   S   N   G   G   G   I   G       60

181 ATA GTG CCC ACA TTA CAA AAT ATT GTT GCT ACG GTG AAT CTT GAT TGT CGA CTT      240
 61  I   V   P   T   L   Q   N   I   V   A   T   V   N   L   D   C   R   L       80

241 AAA ACA ATT GCT TTA CAT GCT AGA AAT GCC GAA TAT AAT CCA AAA CGT TTT GCT GCG GTG  300
 81  K   T   I   A   L   H   A   R   N   A   E   Y   N   P   K   R   F   A   A   V  100

301 ATT ATG AGA ATT AGA GAT CCA AAA ACT ACG GCA TTA ATC TTT GCT TCG GGG AAA ATG GTT  360
101  I   M   R   I   R   D   P   K   T   T   A   L   I   F   A   S   G   K   M   V  120
```

```
361 GTG ACT GGG GCT AAA TCC GAA GAT GAT TCC AAG TTG GCT TCA AGA AAG TAT GCT AGA ATC  420
121  V   T   G   A   K   S   E   D   D   S   K   L   A   S   R   K   Y   A   R   I   140

421 ATT CAA AAG TTG GGG TTC AAT GCT AAA TTT TGT GAT TTT AAA ATT CAA AAT ATA GTG GGG  480
141  I   Q   K   L   G   F   N   A   K   F   C   D   F   K   I   Q   N   I   V   G   160

481 TCA ACA GAT GTT AAG TTT GCT ATT AGA TTA GAA GGC TTA GCT TTT GCT CAT GGT ACT TTC  540
161  S   T   D   V   K   F   A   I   R   L   E   G   L   A   F   A   H   G   T   F   180

541 TCT TCA TAT GAA CCA GAA TTA TTT CCT GGG TTA ATT TAT AGA ATG GTG AAA CCA AAA ATT  600
181  S   S   Y   E   P   E   L   F   P   G   L   I   Y   R   M   V   K   P   K   I   200

601 GTT TTA CTT ATA TTT GTT TCT GGG AAA ATT GTT TTG ACG GGT GCC AAA AAG AGA GAA GAA  660
201  V   L   L   I   F   V   S   G   K   I   V   L   T   G   A   K   K   R   E   E   220

661 ATT TAT GAT GCA TTT GAA CTG ATT TAT CCG GTT TTA AAT GAA TTT CGT AAA AAT TGA      717
221  I   Y   D   A   F   E   L   I   Y   P   V   L   N   E   F   R   K   N   *       239
```

FIG. 2A

```
1   TAAGCTTGTATTACTAAGGATATT ATG TCG CCA TCA ACA TCT ACG GCA GTA CAG GAG TAT ATT GGA    66
1                             M   S   P   S   T   S   T   A   V   Q   E   Y   I   G    14

67  CCA AAC TTG AAT GTT ACA TTA ACA GAG TGT CCT GAG AAG ATA TTT CCA GAT TTG GTA         126
15   P   N   L   N   V   T   L   T   E   C   P   E   K   I   F   P   D   L   V          34

127 GAG AGG TTC AGC GAA GGT GAC ATT GTC TGT GGC AGT TGT GGG CTA GTA TTG AGT GAT CGT     186
35   E   R   F   S   E   G   D   I   V   C   G   S   C   G   L   V   L   S   D   R     54

187 GTT GTG GAT ACG AGA TCA GAA ACT TTC AGT AAC GAT CAA AAT GGT GAT                      246
55   V   V   D   T   R   S   E   W   R   T   F   S   N   D   Q   N   G   D              74

247 CCT TCT CGT GTT GGT GAT GCA GGT AAC CCT TTA TTA GAC ACA GAG GAC TTG TCC ACA ATG     306
75   P   S   R   V   G   D   A   G   N   P   L   L   D   T   E   D   L   S   T   M     94

307 ATT TCT TAT GCT CCT GAT AGT ACC AAA GCA GGA AGA GAG TTA AGC CGA CAA GCC CAA TCT AAA  366
95   I   S   Y   A   P   D   S   T   K   A   G   R   E   L   S   R   A   Q   S   K    114

367 TCT CTA GTC GAT AAA CAA TTG CCT AAA ATA GAC GCA TAT ATC AAG ATT TCT CAA ATG         426
115  S   L   V   D   K   Q   L   P   K   I   D   A   Y   I   K   I   S   Q   M         134

427 TGC GAT GGT TAT GAC GAG GCC AAG GAA GTC TAC AAA ATG                                  486
135  C   D   G   Y   D   E   A   K   E   V   Y   K   M                                  154

487 GTT TAT GAC GAG AAA CCA TTG CGA GGA AAA TCA CAA GAG AGT ATC ATG GCA TCT ATC         546
155  V   Y   D   E   K   P   L   R   G   K   S   Q   E   S   I   M   A   S   I         174
```

```
547  TTT ATT GGT TGC AGA AAG GCC AAT GTT GCT CGT TCA TTC AAA GAG ATA TGG GCA AAG ACT  606
175   F   I   G   C   R   K   A   N   V   A   R   S   F   K   E   I   W   A   K   T   194

607  AAT GTA CCT CGT AAG GAA ATT GGT AAA GTG TTC AAG ATC ATG GAC AAG ATC ATT CGT GAA  666
195   N   V   P   R   K   E   I   G   K   V   F   K   I   M   D   K   I   I   R   E   214

667  AAG AAT GCA GCC AAC CCT AAT GCT GCA TAT TAC GGT CAA GAC AGC ATT CAA ACC ACC CAA  726
215   K   N   A   A   N   P   N   A   A   Y   Y   G   Q   D   S   I   Q   T   T   Q   234

727  ACT TCG GCC GAG GAT TTG ATT AGA AGA TTC TGT TCT CAC TTG GGT GTT AAC ACA CAA GTT  786
235   T   S   A   E   D   L   I   R   R   F   C   S   H   L   G   V   N   T   Q   V   254

787  ACA AAT GGT GCG GAA TAC ATA GCC AGA ACT GTA ATT GCT GAA GTC GGG GTT TTA GCA AGA  846
255   T   N   G   A   E   Y   I   A   R   T   V   I   A   E   V   G   V   L   A   R   274

847  TCG CCA ACT ACA ATT GCT GCA ACT GTA ATT TAC ATG GCT TCA CTA GTG TTT GGA TTT GAC  906
275   S   P   T   T   I   A   A   T   V   I   Y   M   A   S   L   V   F   G   F   D   294

907  TTA CCT CCA TCC AAG ATA TCT GAT AAA GAG GAG AAA ACT GGT GTC AGT GAT CCA ACT TCA  966
295   L   P   P   S   K   I   S   D   K   E   E   K   T   G   V   S   D   P   T   S   314

967  TAC AAG TAC ATG TAC GAG GAG AAA CAA TTG ATT GAT CCA TCT TGG ATA GAA AGT GGT  1026
315   Y   K   Y   M   Y   E   E   K   Q   L   I   D   P   S   W   I   E   S   G   334

1027 AAA GTA AAA TTG GAA AAA ATA CCA AAA AAC TAA TACAGCGGAGTCGCCACTGTTAATCCTTTACCCTCT  1095
335   K   V   K   L   E   K   I   P   K   N   *                                         345
```

TFIIB TRANSCRIPTION FACTOR FROM *CANDIDA ALBICANS* AND METHODS OF SCREENING FOR INHIBITORS OF *CANDIDA ALBICANS* GROWTH

This is a division of application Ser. No. 08/625,377, filed Apr. 1, 1996, now U.S. Pat. No. 5,863,762. Each of these prior applications is hereby incorporated herein by reference, in its entirety.

The invention was made in part using government funds, NIH grant no. GM46498, and therefore the U.S. government has certain rights in the invention.

The invention relates in general to transcription factors and to methods for screening for antifungal agents.

BACKGROUND OF THE INVENTION

The yeast *Candida albicans* (*C. albicans*) is one of the most pervasive fungal pathogens in humans. It has the capacity to opportunistically infect a diverse spectrum of compromised hosts, and to invade many diverse tissues in the human body. It can in many instances evade antibiotic treatment and the immune system. Although *Candida albicans* is a member of the normal flora of the mucous membranes in the respiratory, gastrointestinal and female genital tracts, in such locations, it may gain dominance and be associated with pathologic conditions. Sometimes it produces progressive systemic disease in debilitated or immunosuppressed patients, particularly if cell-mediated immunity is impaired. Sepsis may occur in patients with compromised cellular immunity, e.g., those undergoing cancer chemotherapy or those with lymphoma, AIDS, or other conditions. Candida may produce bloodstream invasion, thrombophlebitis, endocarditis, or infection of the eyes and virtually any organ or tissue when introduced intravenously, e.g., via tubing, needles, narcotics abuse, etc.

*Candida albicans* has been shown to be diploid with balanced lethals, and therefore probably does not go through a sexual phase or meiotic cycle. This yeast appears to be able to spontaneously and reversibly switch at high frequency between at least seven general phenotypes. Switching has been shown to occur not only in standard laboratory strains, but also in strains isolated from the mouths of healthy individuals.

Nystatin, ketoconazole, and amphotericin B are drugs which have been used to treat oral and systemic Candida infections. However, orally administered nystatin is limited to treatment within the gut and is not applicable to systemic treatment. Some systemic infections are susceptible to treatment with ketoconazole or amphotericin B, but these drugs may not be effective in such treatment unless combined with additional drugs. Amphotericin B has a relatively narrow therapeutic index and numerous undesireable side effects and toxicities occur even at therapeutic concentrations. While ketoconazole and other azole antifungals exhibit significantly lower toxicity, their mechanism of action, inactivation of cytochrome $P_{450}$ prosthetic group in certain enzymes, some of which are found in humans, precludes use in patients that are simultaneously receiving other drugs that are metabolized by the body's cytochrome $P_{450}$ enzymes. In addition, resistance to these compounds is emerging and may pose a serious problem in the future.

There is a need in the art for an effective treatment of opportunistic infections caused by *Candida albicans*. Therefore, one object of the invention is to provide screening assays for identifying potential inhibitors of *Candida albicans* growth. Another object of the invention is to provide screening assays and to identify potential inhibitors of *Candida albicans* growth that are based on inhibition of transcription in this organism.

Synthesis of mRNA in eukaryotes requires RNA polymerase II and accessory transcription factors, some of which are general and act at most, if not all, promoters, and others of which confer specificity and control. Five general factors, a, b, d, e, and g, have been purified to homogeneity from the yeast *S. cerevisiae,* and have been identified as counterparts of human or rat factors, TFIIE, TFIIH, TFIID, TFIIB and TFIIF, respectively. These factors assemble at a promoter in a complex with RNA polymerase II to initiate transcription. Binding studies have shown that the order of assembly of the initiation complex on promoter DNA begins with factor d (TFIID), is followed by factor e (TFIIB), and then by polymerase and the remaining factors. Factors b (TFIIH), e (TFIIB) and g (TFIIF), however, bind directly to polymerase II, and as many as four of the five factors may assemble with the polymerase in a holoenzyme before promoter binding. The functional significance of interactions revealed by binding studies is not clear in that only a few percent of initiation complexes may give rise to transcripts.

Many aspects of transcription by RNA polymerase II are conserved between yeast and higher eukaryotes. For example, there is extensive amino acid sequence similarity among the largest subunits of the yeast, Drosophila and mammalian polymerase. Other components of the transcription apparatus, such as TATA-binding and enhancer binding factors, are in some instances interchangeable between yeast and mammalian in vitro binding or transcription systems. There are, nonetheless, significant differences between the two systems. TATA elements are located from 40 to 120 or more base pairs upstream of the initiation site of an *S. cerevistase* promoter, and where these elements occur, they are required for gene expression. The fact that *C. albicans* genes function in *S. cerevisiase* suggests that it also uses the 40 to 120 base pair spacing between the TATA element and initiation site. In contrast, mammalian (as well as *S. pombe*) TATA elements and transcription start sites are only 25 to 30 bp apart, and deletion of a TATA element does not always reduce the frequency of transcription initiation, although it may alter the initiation site. There are also varying degrees of homology between transcription factor sequences from yeast and mammalian sources. Human and *S cerevisiae* TFIIB's have 50–60% amino acid sequence identity, and also are not species interchangeable in supporting cell growth. Some of the multisubunit factors, such as RNA polymerase II, TFIIF and TFIID, contain different numbers of subunits in humans and yeast. The molecular weights of corresponding polypeptides differ in humans and yeast with sequences being present in a given yeast factor that are not present in its human counterpart, and vice versa.

Operative substitution of the same transcription factor in transcription systems of different yeast strains is not predictable. This is true despite a high degree of amino acid sequence identity among some transcription factors from different yeast strains. For example, the ability of a given transcription factor to support efficient and accurate transcription in a heterologous yeast strain is not predictable. Li et al. (1994, Science 263:805) tested the interchangeability of *S. cerevisiae* and *S. pombe* transcription factors in vitro, and report that many *S. cerevisiae* components cannot substitute individually for *S. pombe* transcription factors a, e, or RNA polymerase II, but combinations of these components were effective. In one instance, active transcription could not be reconstituted when *S. cervisiae*-derived TFIIB was the sole substitution into a TFIIB-depleted set of factors from *S. pombe*. A TFIIB-RNA polymerase II combination from *S. cerevisiae* was able to substitute, indicating that the functional interaction of these two components is not only important, but also that the activity may be dependent on species-specific determinants that cannot be complemented by either component derived from a different organism. The unpredictability in making substitutions of a given factor among different yeast strains is also evident in that such substitutions are not reciprocal; that is, substitutions of *S. pombe* fractions into an *S. cerevisiae* transcription system are less effective than the reverse substitutions (Li et al., supra).

The yeast *Candida albicans* differs from most yeast strains in that it does not use the same genetic code that most organisms, whether mammalian or yeast, utilize. Santos et al. (1995, Nucleic Acids Research, 23:1481) report that the codon CUG, which in the universal code is read as a leucine, is decoded as a serine in Candida. Therefore, any CUG codon that is decoded in *Candida albicans* as a serine, would be decoded as a leucine in the transformed *S. cerevisiae*. Any gene containing a CUG codon would therefore be translated as different amino acid sequences in *Candida albicans* and *S. cerevisiae*. Such mistranslation may produce an inactive protein, since the amino acids serine and leucine have markedly different chemical properties and serine is known to be an essential residue in the active site of some enzymes. Replacement of leucine by serine at CUG encoded residues is a serious problem in the use of many reporter systems (e.g., β-galactosidase, Chloramphenicol acetyltransferase, Flux) in *Candida albicans*. Previous experiments have shown that translation by Candida of CUG as serine instead of leucine often resulted in the production of inactive reporter proteins.

Another object of the invention is to provide an assay for screening for selective inhibition of *Candida albicans* growth and/or viability.

Yet another object of the invention is to provide a molecular target for inhibition of *Candida albicans* transcription or transcription initiation.

SUMMARY OF THE INVENTION

The invention encompasses a recombinant nucleic acid comprising a nucleic acid sequence encoding *Candida albicans* TFIIB.

The invention also encompasses a vector comprising a nucleic acid sequence encoding *Candida albicans* TFIIB, and a transformed host cell containing a nucleic acid sequence encoding *Candida albicans* TFIIB.

The invention also encompasses a recombinant polypeptide comprising *Candida albicans* TFIIB, and a fragment of *Candida albicans* TFIIB, the fragment being characterized in that it inhibits the biological activity of *Candida albicans* TFIIB in transcription initiation, or prevents the growth of *Candida albicans*.

The invention also encompasses a method for producing recombinant *Candida albicans* TFIIB, comprising culturing a host cell transformed with a nucleic acid encoding *Candida albicans* TFIIB under conditions sufficient to permit expression of the nucleic acid encoding *Candida albicans* TFIIB, and isolating *Candida albicans* TFIIB.

The invention also encompasses a screening method for identifying an inhibitor of *Candida albicans* growth, comprising detecting inhibition of mRNA transcription in an in vitro transcription assay comprising a DNA template, RNA polymerase II, recombinant *Candida albicans* TFHB, and a candidate inhibitor, wherein production of an mRNA transcript complementary to the DNA template occurs in the absence of the candidate inhibitor. Preferably, the assay will also include *C. albicans* TBP.

The invention also encompasses a screening method for identifying an inhibitor of *Candida albicans* growth, comprising detecting in the presence of a candidate inhibitor inhibition of formation of a complex comprising a DNA template recombinant *Candida albicans* TFIIB and TBP, wherein in the absence of the candidate inhibitor, formation of the complex occurs.

The invention also encompasses a screening method for identifying an inhibitor of *Candida albicans* growth, comprising detecting in the presence of a candidate inhibitor inhibition of formation of a complex comprising *Candida albicans* TFIIB and *Candida albicans* TBP, wherein in the absence of the candidate inhibitor formation of the complex occurs. Preferably, the complex will include a DNA template.

The invention also encompasses a screening method for identifying an inhibitor of *Candida albicans* growth, comprising detecting in the presence of a candidate inhibitor inhibition of formation of a complex comprising RNA polymerase II, *Candida albicans* TBP, and *Candida albicans* TFIIB, wherein in the absence of the candidate inhibitor formation of the complex occurs. Preferably, the complex may also include a DNA template; and RNA polymerase II from *C. albicans*.

In the above-described screening methods, detection may be performed in the presence of a plurality of candidate inhibitors. In screening methods of the invention which involve screening of a plurality of candidate inhibitors, the plurality of inhibitors may be screened together in a single assay or individually using multiple simultaneous individual detecting steps.

The invention also encompasses a method of preventing *Candida albicans* growth in culture, comprising contacting the culture with an inhibitor that selectively inhibits the biological activity of *Candida albicans* TFIIB.

The invention also encompasses a method of preventing *Candida albicans* growth in a mammal, comprising contacting the mammal with an inhibitor that selectively inhibits the biological activity of *Candida albicans* TFIIB.

As used herein, "inhibition" refers to a reduction in the parameter being measured, whether it be *Candida albicans* growth or viability, *Candida albicans* TFIIB-mediated transcription, or formation of a *Candida albicans* TFIIB transcription complex. The amount of such reduction is measured relative to a standard (control). Because of the multiple interactions of *Candida albicans* TFIIB in transcription initiation, the target product for detection varies with respect to the particular screening assay employed. Three preferred detection products presented in this disclosure are; a) newly transcribed mRNA, b) a DNA-TFIIB complex, and c) a TBP-TFIIB-RNA polymerase complex. "Reduction" is defined herein as a decrease of at least 25% relative to a control, preferably of at least 50%, and most preferably of at least 75%.

As used herein, "growth" refers to the normal growth pattern of *Candida albicans*, i.e., to a cell doubling time of 60–90 minutes. "Viability" refers to the ability of *Candida albicans* to survive in culture for 48 hours.

"Biological activity" refers to the ability of TFIIB to form a transcription complex with a DNA template or other proteins of the transcription complex, or to interact with other transcription components so as to permit initiation of transcription.

"DNA template" refers to double stranded DNA and, where indicated by the particular binding assay to single stranded DNA, at least 10 nucleotides in length, that may be negatively supercoiled, possesses a promoter region, and contains a yeast TATA consensus region upstream of the promoter. DNA templates useful herein preferably contain a TATA sequence that is located from 40 to 120 or more base pairs upstream of the initiation site (distance measured from the first T of the TATA element to the 5'-most initiation site). An especially efficient DNA template for use in methods of the invention involving transcription is devoid of guanosine residues, and therefore a "G-minus" or "G-less" cassette is preferred (Sawdago and Roeder, 1985, PNAS 82:4394–4398).

"MRNA transcript" refers to a full-length transcript as well as to truncated transcripts, oligonucleotide transcripts and dinucleotide RNAs.

"Formation of a complex" refers to the binding of TFIIB to other transcription factors (i.e., protein-protein binding) as well as to binding of TFIIB to a DNA template; such binding will, of course, be a non-covalent association.

Other features and advantages of the invention will be apparent from the description, preferred embodiments thereof, the drawings, and from the claims.

BRIEF DESCRIPTION OF THE DRAWINGS

FIGS. 1A and 1B presents the nucleotide and amino acid sequences of the *Candida albicans* transcription factor TBP, SEQ ID NO:1 and SEQ ID NO:2, respectively.

FIGS. 2A and 2B presents nucleotide and amino acid sequence of the *Candida albicans* transcription factor TFIIB, SEQ ID NO:3 and SEQ ID NO:4, respectively.

DESCRIPTION

The invention is based on the discovery of a novel protein, *Candida albicans* TFIIB, and on the isolation of recombinant DNA encoding *Candida albicans* transcription factor TFIIB. Because TFIIB is essential for viability of the cell, a compound that blocks the biological activity of the protein is expected to have fungicidal properties. Therefore, the invention is also based on the development of assays for screening from inhibitors of TFIIB.

Isolation and Characterization of the *Candida albicans* TBP and TFIIB Genes

Given the unpredictability with respect to operative substitutions of a given transcription factor among different yeast strains, one cannot assume that strategies for cloning of the gene encoding a given transcription factor which are based on factor function, such as genetic complementation, will work. Other cloning strategies, which do not require functional complementation, such as those based on homology at the nucleic acid level, may be utilized in an attempt to circumvent a requirement for factor function. For example, Southern hybridization of specific sequences to a library carried in *E. coli* and PCR amplification of potentially highly homologous regions of a gene are two strategies that have been successfully used to clone homologous genes from different organisms. To ascertain the likelihood of success of these or similar methods, we performed a Southern hybridization experiment where a radiolabeled probe containing the entire *S. cerevisiae* coding sequence of TBP (SPT15) was hybridized to genomic DNA preparations from *S. cerevisiae* and *Candida albicans* that were digested with various restriction enzymes. At low stringency (0.2X SSC, room temperature hybridization) the probe efficiently hybridized as expected to known restriction bands in the *S. cerevisiae* digests, but did not detectably hybridize to any restriction band of the *Candida albicans* digests. The Saccharomyces sequences were detectable on an autoradiograph with less than 10 minutes of exposure. By contrast, even with one week of exposure, there was no detectable hybridization of the same probe to the *Candida albicans* DNA The conclusion from these observations is that it is likely that the DNA sequence of the *Candida albicans* gene had diverged quite significantly from the *S. cerevisiae* sequence, and thus Southern hybridization, PCR strategies or other cloning methods based on hybridization of complementary nucleic acid sequences are unlikely to lead to cloning of the *Candida albicans* homolog of SPT15.

The approach used to clone the *Candida albicans* homolog of TFIIB involved genetic complementation of mutant *S. cerevisiae* strains. A library of *Candida albicans* genomic sequences was introduced into a strain of *S. cerevisiae* that contained a mutated TFIIB gene (SUA7). This mutant strain was capable of growth at 30° C., but was non-viable at 37° C., due to a temperature sensitive mutation in the TFIIB gene. Following transformation of the library into the strain, the cells were grown at 37° C., and the colonies which grew at this non-permissive temperature were further studied as potentially carrying a *Candida albicans* homolog of the defective gene. Plasmids were purified from the various isolates which were viable at 37° C. After candidate clones were isolated by growth at the nonpermissive temperature, the library plasmid was recovered from the cell and retested to confirm that the *C. albicans* sequences on the plasmid were substituting for the *S. cerevisiae* gene. Subclones of *C. albicans* sequences were constructed by standard cloning methods, and the minimal Candida DNA sequence that substituted was sequenced using standard methods. Digestion of these plasmids revealed a common DNA fragment approximately 1.35 kb in length, which when subcloned into pRS316 proved to complement multiple independent SUA7 strains of *S. cerevisiae*. This DNA fragment was sequenced, and confirmed *C. albicans* SUA7 sequence homology to *S. cerevisiae* SUA7.

The nucleotide sequence encoding *Candida albicans* TBP and the predicted amino acid sequence of the encoded protein are presented in FIGS. 1A and 1B (SEQ ID NOS: 1 and 2). The nucleotide sequence encoding *Candida albicans* TFIIB and the predicted amino acid sequence of the encoded protein are presented in FIGS. 2A and 2B (SEQ ID NOS: 3 and 4).

Methods For Screening Potential Inhibitors of *Candida albicans* Growth and/or Viability Because TFIIB is essential for transcription initiation, the recombinant *Candida albicans* TFIIB gene and recombinant protein encoded by this gene may be utilized in screening assays for inhibitors of *Candida albicans* growth and viability. The screening assays of this invention detect inhibition of the *Candida albicans* TFIIB-mediated transcription initiation, either by measuring inhibition of transcription, transcription initiation, or initiation complex formation, or by assaying formation of a protein/DNA or a protein/protein complex.

EXAMPLE 1

Screening for Inhibitors of Transcription a) Transcription Assay Components.

An in vitro transcription assay consisting of the minimal components necessary to synthesize an mRNA transcript from a DNA template can be used to screen for inhibition of mRNA production. The elements of such an assay consist of; a) a DNA template, b) RNA polymerase II, c) recombinant *Candida albicans* TFIIB, and d) a TBP which is preferably *Candida albicans* TBP. In order to increase the efficiency of transcription, additional components of the transcription complex may be included, as desired; e.g., TFIIE, TFIIF, TFIIH, etc.

Parvin and Sharp (*Cell* 73, 533–540, 1993) have reconstituted gene transcription in vitro with a minimal reaction containing a DNA template, RNA polymerase II, TFIIB, and TBP. For efficient transcription under minimal conditions, the DNA template (a) is supercoiled, and (b) possesses a promoter region containing a TATA consensus region. Additionally, Lue et al. (*Science* 246, 661–664, 1989) have determined that transcription may be detected most efficiently with a DNA template devoid of guanosine residues (a G-minus or G-less cassette). Promoter dependence is demonstrated by the loss of signal when a plasmid lacking promoter sequences is utilized as a template. Correct initiation is demonstrated by the production of a band with a mobility consistent with the size of the expected product on denaturing polyacrylamide electrophoresis gels.

As stated above, *Candida albicans* TFIIB forms a transcription initiation complex with RNA polymerase II. Therefore, it is desired that an in vitro transcription assay according to the invention contain RNA polymerase II. Although it is possible to perform an inhibitor screening assay using RNA polymerase II from a yeast strain other than *Candida albicans*, e.g., *S. cerevisiae*, it is most desirable to use a homologous assay in which the transcription complex components are from *Candida albicans*.

A method for *S. cerevisiae* RNA polII purification is described in Edwards et al. (*Proc. Natl. Acad Sci. USA* 87: 2122–2126 (1990)). Alternatively, highly purified RNA polymerase II from *Candida albicans* was provided as follows.

RNA polymerase II activity was measured in reactions containing 50 mM Tris-Cl, pH 7.9 (4° C.), 50 mM $(NH_4)_2 SO_4$, 2.5 mM $MnCl_2$, 0.1 mM EDTA, 5 mM DTT, 100 μg/ml BSA, 0.6 mM ATP, CTP and GTP, 25 μM UTP (2.5μ Ci) [α-$^{33}$P] UTP and 100 μg/ml heat-denatured calf thymus DNA in a final volume of 50 μl. Reactions were incubated for 60 min. at 30° C. and terminated by addition of 50 μl 15% (w/v) trichloroacetic acid. Acid-insoluble radioactivity was collected by filtration through glass fiber filters and quantified by liquid scintillation spectrophotometry. One unit of RNA polymerase activity catalyzes the incorporation of 1 pmol of UTP into acid-insoluble material in 60 min. under the conditions described above.

Candida albicans was obtained from the American Type Culture Collection (ATCC 10231) and cultured in YPD medium (Current Protocols in Molecular Biology, Vol. 2, 13, Suppl. 19 (1989)) at 30° C. with vigorous agitation and aeration. All procedures were carried out at 4° C. using 18 liter cultures. Cells were harvested by centrifugation (5000 rpm, 10 min., Sorvall H6000 rotor), washed once with ~1l. ice-cold deionized water and repelleted as above. The cell pellet (200–300 g wet weight) was thoroughly resuspended in a volume of Buffer A (50 mM Tris-HCl, pH 7.9, 40° C., 10% glycerol, 1 mM EDTA, 5 mM $MgCl_2$, and protease inhibitor) containing 300 mM $(N_4H_2) S_4O$ equivalent to the packed volume of cells (determined by weight assuming a density of 1 g/ml cells). Resuspended cells were either processed immediately as described below or frozen by pipetting into liquid $N_2$ and stored at –80 C. Frozen cells were thawed on ice prior to proceeding. Following the addition of NP-40 to a final concentration of 0.1%, cells were disrupted by grinding with 1 ml acid-washed glass beads/ml cell suspension (Sigma, 400–625 μM) using 12 bursts of 30 sec. each in a Bead Beater (BioSpec). Glass beads were allowed to settle out and the supernatant was centrifuged at 30,000×g for 40 min. Solid $(NH_4)_2 SO_4$ was slowly added to a final concentration of 0.4 g/ml supernatant and the resulting precipitate was pelleted by centrifugation at 100,000× g for 30 min. The pellet was resuspended with a volume of Buffer A sufficient to yield a conductivity equivalent to Buffer A containing 75 mM $(NH_4)_2 SO_4$.

Following centrifugation of the resuspension at 10,000× g for 10 min, this supernatant ~ 1–1. 5 mg protein/ml) was loaded onto a 300 ml DE-52 DEAE-cellulose column equilibrated with Buffer A containing 75 mM $(NH_4)_2 SO_4$. After washing with 5 column volumes Buffer A containing 75 mM $(NH_4)_2 SO_4$, and 5 column volumes Buffer A containing 0.15 M $(NH_4)_2 SO_4$, RNA polymerase II was eluted with 5 column volumes Buffer A containing 0.4 M $(NH_4)_2 SO_4$. Fractions were collected containing the peak of protein, determined by absorbance at 280 nm and pooled. The pool was dialyzed against Buffer A containing 20% glycerol for 3 hr. at 4° C.

The 0.4 M $(NH_4)_2 SO_4$ eluate from DEAE-cellulose (261 mg protein, 290 ml) was diluted with sufficient Buffer A to lower the conductivity to the equivalent of Buffer A containing 0.15 M $(NH_4)_2 SO_4$, centrifuged at 10,000× g for 10 min. and the supernatant was loaded at a flow rate of 30 ml/hr onto an 30 ml DEAE-cellulose column equilibrated with Buffer A containing 0.15 M $(NH_4)_2 SO_4$. After washing with 3 column volumes of Buffer A containing 0.15 M $(NH_4)_2 SO_4$, the column was developed with a 200 ml linear gradient of 0.15–0.4 M $(NH_4)_2 SO_4$ in Buffer A at a flow rate of 45 ml/hr. Fractions from the single peak of amanitin-sensitive RNA polymerase activity, eluting around 0.22 M $(NH_4)_2 SO_4$, were pooled (21.1 mg protein, 45 ml) and loaded directly onto a 5 ml Heparin agarose column equilibrated with Buffer A containing 0.2 M $(NH_4)_2 SO_4$. The column was washed with 3 column volumes of Buffer A containing 0.2 M $(NH_4)_2 SO_4$ and developed with an 80 ml linear gradient of 0.2–0.6 M $(NH_4)_2 SO_4$ in Buffer A. The active fractions, which eluted at approximately 0.42 M $(NH4)_2SO_4$ were pooled (2.0 mg protein, 15 ml), frozen in 300 μl aliquots in liquid $N_2$, and stored at –80° C. where activity was stable for at least 6 months.

Purification of protein initiation factors used in the assay is accomplished by standard methods known in the art (e.g., phosphocellulose chromatography followed by gel filtration), as described in (*Nature* 346, 387–390 (1990)).

To screen for *Candida albicans* TFIIB-mediated transcription inhibition, a transcription assay is reconstituted using recombinant *Candida albicans* TFIIB. *Candida albicans* TFIIB is expressed in and purified from *E. coli* as described in Buratowski, 1993, *Proc. Natl. Acad Sci.* 90:5633. Supercoiled plasmid DNA containing the CYC1 promoter linked to the G-less cassette described by Lue et al. (*Science* 246, 661–664 (1989)), is purified by standard methods for purification of supercoiled circular DNA (Current Protocols in Molecular Biology, Vol. 2, 13, Suppl. 19 (1989)). 10–100 ng of *Candida albicans* TFIIB, 10–100 ng of *Candida albicans* TBP, 10–100 ng *Candida albicans* RNA polymerase II and 1 μg plasmid DNA are added to 50 μl reaction mixtures containing 50 mM HEPES, pH 7.5, 10% glycerol, 90 mM potassium glutamate, 0.75% polyethylene glycol (molecular weight 3350), 10 mM magnesium acetate, 5 mM EGTA, 5 mM DTT, 0.4 mM ATP, 0.4 mM CTP, 10 µM [α-$^{32}$P]UTP, 0.2 mM 3'-O-methyl-GTP, and containing or lacking a candidate inhibitor molecule. Reactions are incubated at 30° C. for 30–60 min. and RNA synthesis is detected as described below.

b) Detection of Transcribed RNA.

The detection of newly transcribed RNA is achieved by standard methods (Current Protocols in Molecular Biology, Vol. 1, 4.10, Suppl 24 (1989)). As one example, RNA synthesis can be detected as incorporation of a radioactively or fluorescently labeled nucleotide into higher molecular weight RNA products, determined by one of the following methods: 1) acid-insoluble labeled material quantitated by the appropriate method (e.g. scintillation counting for radioactive precursors, fluorometry for fluorescent precursors); 2) labeled reaction product that hybridizes to oligonucleotides complementary to the correctly initiated transcript (i.e., northern blot analysis); 3) the presence of a labeled band with the appropriate mobility detected by autoradiography, on denaturing polyacrylamide electrophoresis gels: 4) any other method that discriminates mononucleotides from polynucleotides, where polynucleotides are the desired RNA product. Such methods may utilize one or more well known techniques of molecular biology (Current Protocols in Molecular Biology, Vol. 2, 13, Suppl. 19 (1989)), for example; UV analysis; affinity systems (e.g., affinity chromatography, nitrocellulose filtration, biotin/streptavidin systems, immunoaffinity,) (Current Protocols in Molecular Biology, Vol.2, 13, Suppl. 19 (1989)); and high performance liquid chromatography.

The inclusion of an inhibitor molecule that interferes with *Candida albicans* TFIIB biological activity inhibits transcription. In this assay inhibition is measured as a reduction in the amount of mRNA transcript produced relative to the amount of mRNA transcript produced in the absence of the inhibitor (the positive control). A decrease in amount of mRNA transcript is indicative of an inhibitor. The determination of effective levels of mRNA transcript inhibition is described below.

EXAMPLE 2

Screening for Inhibition of DNA-Protein Complex Formation

A DNA-protein binding assay consisting of the minimal components necessary to permit DNA-*Candida albicans* TFIIB association to occur can be used to screen for inhibition of the formation of the DNA-TBP-*Candida albicans* TFIIB complex during transcription initiation. The components of such an assay include: a) a DNA template, b) recombinant *Candida albicans* TFIIB, c) TBP, preferably from *C. albicans,* and optionally d) a candidate *Candida albicans* TFIIB inhibitor.

The inclusion of an inhibitor molecule that interferes with the interaction between the *Candida albicans* TFIIB and the DNA template inhibits transcription initiation. The inhibitor may interact directly with the *Candida albicans* TFIIB protein, and/or it may interact with TBP and/or with the DNA template at the site of TFIIB/TBP binding. In this assay inhibition is measured as a reduction in the amount of DNA-TBP-TFIIB complex produced relative to the amount of DNA-TBP-TFIIB complex produced in the absence of the inhibitor (the positive control). A decrease in the amount of DNA-TBP-TFIIB complex is indicative of an inhibitor. Determination of effective levels of DNA-TBP-TFIIB inhibition is described below.

One DNA binding assay is constructed as follows. 10–100 ng *Candida albicans* TFIIB, expressed in and purified from *E. coli* as described above, is incubated with 0.5 ng labeled (e.g. radioactively or fluorescently labeled) oligonucleotide containing a TATA element such as the one described by Buratowski et al. (*Cell* 56, 549–561 (1989)) and 10–100 ng *Candida albicans* TBP in reactions containing 10–20 mM HEPES (or equivalent), pH 7.5–8.0, 5 mM MgCl$_2$, 12% glycerol, 10 mM dithiothreitol (DTT), 100 µg/ml BSA, 5–20 µg/ml poly (dG-dC):(dG-dC) and a candidate inhibitor of complex formation. Reactions are incubated at 30° C. for 30–60 min.

Formation of a DNA-TBP-TFIIB complex may be detected as retention of labeled DNA (the label being detected by an appropriate methodology such as scintillation counting for radiolabeled DNA or fluorometry for fluorescently labeled DNA) utilizing known affinity methods for protein immobilization (e.g., biotin/streptavidin, nitrocellulose filtration, affinity chromatography, immunoaffinity). Nonretention of labeled DNA due to the failure of *Candida albicans* TFIIB-TBP-DNA complex formation is indicative of an effective inhibitor.

Complex formation may also be detected as retention of labeled *Candida albicans* TFIIB (e.g. radioactively, fluorescently) utilizing known methods for immobilizing DNA. Nonretention of labeled *Candida albicans* TFIIB due to the failure of *Candida albicans* TFIIB-TBP-DNA complex formation is indicative of an effective inhibitor. The preceding two methods are suitable for high-throughput chemical compound library screening applications such as those commonly used in drug discovery.

A third example of detecting DNA/protein complex formation involves detection of an electrophoretic mobility shift of labeled DNA on 4% polyacrylamide gels containing 5% (v/v) glycerol, 25 mM Tris, 100 mM glycine, 1 mM EDTA, 5 mM MgCl$_2$, pH 8.3 in the presence of *Candida albicans* TFIIB and TBP. The position of the labeled oligonucleotide is detected by appropriate methods (e.g., autoradiography for radioactive oligonucleotide). The absence or deviation of the expected mobility shift due to DNA-*Candida albicans* TFIIB complex formation is indicative of an effective inhibitor.

Finally, other methods for detecting or separating DNA-protein complexes may be used, including UV crosslinking analysis, high performance liquid chromatography, phage display technology (U.S. Pat. No. 5,403,484. Viruses Expressing Chimeric Binding Proteins), and surface plasmon resonance (Biacore, Pharmacia Biosensor, North America) as described below.

EXAMPLE 3

Screening for Inhibition of Protein-Protein Complex Formation

A protein-protein binding assay consisting of the minimal components necessary to permit *Candida albicans* TBP-*Candida albicans* TFIIB binding to occur can be used to screen for inhibition of the formation of the *Candida albicans* TBP-*Candida albicans* TFIIB complex during transcription initiation. The elements of such an assay consist of a) recombinant *Candida albicans* TFIIB, b) TBP, preferably a recombinant *Candida albicans* TBP, and optionally c) a candidate inhibitor of binding.

The inclusion of an inhibitor molecule that interferes with the interaction between the *Candida albicans* TBP and *Candida albicans* TFIIB inhibits transcription initiation. The inhibitor may interact with the *Candida albicans* TBP or TFIIB protein and thus induce a conformational change which prevents binding, or it may directly inhibit the interaction of *Candida albicans* TFIIB and TBP proteins. In this assay, inhibition is measured as a reduction in the amount of *Candida albicans* TBP-TFIIB complex produced relative to the amount of *Candida albicans* TBP-TFIIB complex produced in the absence of the inhibitor (the positive control). A decrease in the amount of TFIIB-TBP complex is indicative of an inhibitor. Determination of effective levels of inhibition of *Candida albicans* TBP-TFIIB binding is described below.

One assay for formation of *Candida albicans* TBP-TFIIB complex is provided as follows. 10–100 ng *Candida albicans* TFIIB and 10–100 ng *Candida albicans* TBP are expressed in and purified from *E. coli* as described above, and are added to reactions containing 10–20 mM HEPES (or equivalent), pH 7.5–8.0, 5 mM $MgCl_2$, 12% glycerol, 10 mM dithiothreitol (DTT) 100 µg/ml BSA, and a candidate inhibitor. The mixture is then incubated at 30° C. for 30–60 min.

Formation of a complex comprising *Candida albicans* TBP and *Candida albicans* TFIIB may be detected by an electrophoretic mobility shift of labeled (e.g. radioactive or fluorescent) TBP or TFIIB on 4% polyacrylamide gels containing 5% (v/v) glycerol, 25 mM Tris, 100 mM glycine, 1 mM EDTA, 5 mM $MgCl_2$, pH 8.3 in the presence of the unlabeled partner. The position of the labeled partner is detected by appropriate methods (e.g., autoradiography for radioactive oligonucleotide). The absence or deviation of the expected mobility shift due to *Candida albicans* TFIIB-TBP complex formation is indicative of an effective inhibitor.

Formation of a complex comprising *Candida albicans* TBP and *Candida albicans* TFIIB may be detected as retention of labeled TBP utilizing known affinity methods for immobilizing the *Candida albicans* TFIIB protein (e.g., biotin/streptavidin, nitrocellulose filtration, affinity chromatography, immunoaffinity). The failure of formation of the *Candida albicans* TFIIB-TBP complex is indicative of inhibition, and is indicated by nonretention of labeled TBP. Alternatively, the immobilized element may be *Candida albicans* TBP and the labeled partner *Candida albicans* TFIIB.

In the above example, a stronger signal may be conferred in the presence of both TBP and TFIIB and, in addition, a DNA template containing a TATA element. The complex is then quantitated by autoradiography, Phosphorimager technology, or scintillation counting for radioactively labeled factors, fluorometry for fluorescently labeled factors, luminometry for factors labeled with ligands that are detected using chemiluminescent or phosphorescent probing methodologies, or other similar detection methods or materials labeled as described above that are standard in the art.

Other methods for detecting or separating protein-protein complexes may be used, including UV crosslinking analysis, high performance liquid chromatography, phage display technology, and surface plasmon resonance as described herein.

EXAMPLE 4

Assay for Formation of TBP-TFIIB-RNA Polymerase II-DNA Complex

Formation of a TBP, TFIIB, RNA polymerase II, DNA complex is known to be markedly stimulated by the addition of another factor, TFIIF. Previous data indicates that TFIIF from *S. cerevisiae* can function in species as distantly related as *Schizosaccharomyces pombe* and humans, strongly suggesting that this factor can functionally replace its *C. albicans* homolog. Accordingly, this factor is purified from *S. cerevisiae* by published methods (Sayre, 1992, J. Biol. Chem. 267:23383) and used to reconstitute formation of a complex containing *C. albicans* TBP, TFIIB, RNA polymerase II and promoter containing DNA such as that described for reconstitution of the TFIIB-TBP-DNA complex.

Complex formation is carried out in reactions containing, for example, 10–100 ng *Candida albicans* TBP, 10–100 ng *Candida albicans* TFIIB, 10–100 ng *Candida albicans* RNA polymerase II, 10–100 ng *S. cerevisiae* TFIIF, 0.5 ng double-stranded TATA element containing-oligonucleotide (same as that used for TFIIB-TBP-DNA complex assay), 10–20 mM HEPES (or equivalent), pH 7.5–8.0, 5 mM $MgCl_2$, 12% glycerol, 10 mM dithiothreitol (ITT), 100 µg/ml BSA, 5–20 µg/ml poly (dG-dC); (dG-dC) and compound(s) to be tested for inhibitory activity. Following incubation at 30° C. for 30–60 min, complexes are detected by one of the methods described above for the TBP-TFIIB-DNA complex. The TBP-TFIIB-RNA polymerase II-DNA complex has a slower electrophoretic mobility than the TBP-TFIIB-DNA complex identified by using the electrophoretic method. In addition, complex formation can be detected as TBP, TFIIB-dependent retention of RNA polymerase II activity (measured by incorporation of labeled nucleotide precursors into acid-insoluble product using the assay for RNA polymerase activity described in the RNA polymerase II purification protocol above) on a matrix with bound TATA-element containing DNA. The $IC_{50}$ of inhibitory compounds will be determined by titration into reactions reconstituted as described above. The $IC_{50}$ of these compounds against reactions reconstituted with human TBP, TFIIB and RNA polymerase II will also be determined by the same method. Human RNA polymerase II and TFIIF are purified as described previously (Flores et al., 1990, J. Biol. Chem. 265:5629–5634; Reinberg et al., J. Biol. Chem 262:3310–3321). Those compounds whose $IC_{50}$ against reactions containing *C. albicans* factors is ≦⅓ of their $IC_{50}$ against reactions reconstituted with human factors will be tested for their ability to inhibit *C. albicans* growth as described below.

EXAMPLE 5

Phage Display Inhibitor Screening

In addition to the above mentioned standard techniques of the art, other technologies for molecular identification can be employed in the identification of inhibitor molecules. One of these technologies is phage display technology (U.S. Pat. No. 5,403,484. Viruses Expressing Chimeric Binding Proteins). Phage display permits identification of a binding protein against a chosen target. Phage display is a protocol of molecular screening which utilizes recombinant bacteriophage. The technology involves transforming bacteriophage with a gene that encodes an appropriate ligand (in this case, a candidate inhibitor) capable of binding to the target molecule of interest. For the purposes of this disclosure, the target molecule may be *Candida albicans* TFIIB, or a DNA-protein or protein-protein complex formed using TBP and/or TFIIB, as described herein. The transformed bacteriophage (which preferably is tethered to a solid support) express the candidate inhibitor and display it on their phage coat. The cells or viruses bearing the candidate inhibitor which recognize the target molecule are isolated and amplified. The successful inhibitors are then characterized.

Phage display technology has advantages over standard affinity ligand screening technologies. The phage surface displays the microprotein ligand in a three dimensional conformation, more closely resembling its naturally occurring conformation. This allows for more specific and higher affinity binding for screening purposes.

EXAMPLE 6

Biospecific Interaction Analysis

A second relatively new screening technology which may be applied to the inhibitor screening assays of this invention is biospecific interaction analysis (BIAcore, Pharmacia Biosensor AB, Uppsala, Sweden). This technology is described in detail by Jonsson et al. (Biotechniques 11:5, 620–627 (1991)). Biospecific interaction analysis utilizes surface plasmon resonance (SPR) to monitor the adsorption of biomolecular complexes on a sensor chip. SPR measures the changes in refractive index of a polarized light directed at the surface of the sensor chip.

Specific ligands (i.e., candidate inhibitors) capable of binding to the target molecule of interest (i.e., *Candida albicans* TFIIB or a protein-protein or protein-DNA complex containing TFIIB) are immobilized to the sensor chip. In the presence of the target molecule, specific binding to the immobilized ligand occurs. The nascent immobilized ligand-target molecule complex causes a change in the refractive index of the polarized light and is detected on a diode array. Biospecific interaction analysis provides the advantages of; 1) allowing for label-free studies of molecular complex formation; 2) studying molecular interactions in real time as the assay is passed over the sensor chip; 3) detecting surface concentrations down to 10 pg/mm$^2$; detecting interactions between two or more molecules; and 4) being fully automated (Biotechniques 11:5, 620–627 (1991)).

EXAMPLE 7

High Throughput Screening of Potential Inhibitors

It is contemplated according to the invention that the screening methods disclosed herein encompass screening of multiple samples simultaneously, also referred to herein as 'high throughput' screening. For example, in high throughput screening, from several hundred to several thousand candidate inhibitors may be screened in a single assay. An example of high throughput screening assay useful according to the invention is as follows.

A protein A (pA)- *Candida albicans* TFIIB fusion protein is generated by inserting the coding sequence of TFIIB in frame downstream of the pA coding sequence of the plasmipRIT2T (Pharmacia Biotech). The fusion construct is induced, and the resultant recombinant protein is extracted and purified according to the manufacturer's recommended conditions. This procedure can also be carried out for the preparation of a pA- *Candida albicans* TBP fusion protein except that the downstream coding sequence is that of TBP protein; all other steps would remain the same.

A Dynatech Microlite 2 microtiter plate, or equivalent high protein-binding capacity plate, is coated with 1 µg/well human IgG by incubating 300 µl 3.33 µg/ml human IgG (Sigma) in coating buffer (0.2 M sodium carbonate, pH 9.4) in the well for 4–12 hr at 4° C. The coating buffer is then decanted and the wells are washed five times with 300 µl PBS. 300 µl blocking buffer (SuperBlock™ blocking buffer, Pierce) containing 3.33 µg/ml pA-TFIIB or pA-TFIIB are added and the plate is incubated for 4 or more hours at 4° C. The plates may be stored in this form at 4° C. until ready for use. When ready for use the plates are washed five times with 300 µl PBS. Test compound at a final concentration of 20–200 µM and labeled TFIIB or TBP (i.e., nonfusion protein), whichever is not added during the coating step, and 10–1000 fmol DNA containing a TATA sequence, are suspended in HEG buffer containing 200 µg/ml BSA in a total volume of 150 µl and are added and the reaction is incubated at room temperature with gentle agitation for 60 min. The plate is then washed five times with PBS using a Dynatech plate washer or equivalent. Bound labeled protein is quantitated by adding 250 µl Microscint (Packard) per well and is counted in a microtiter plate-compatible scintillation spectrophotometer.

As an alternative, the protein A fusion and the second, non-fusion protein can be incubated in the presence of test compound in polypropylene microtiter plates under the same buffer and incubation conditions described above. The reaction mix is then transferred to the wells of a microtiter plate coated with human IgG (which is prepared as described above, and is stored in blocking buffer and is washed five times with 300 µl PBS immediately before use) and is incubated for 60 min at room temperature with gentle agitation. Retention of radioactive protein is quantified as above.

Interaction of TBP and TFIIB, which is measured as retention of radioactivity on the plate, is dependent on human IgG coating the plate and wild-type *Candida albicans* TBP or TFIIB, one of which must be fused to pA. Candidate inhibitors or extracts that inhibit retention of radioactivity by more than 30% are identified and the inhibitory activity is further purified if necessary.

Inhibitors identified as described above are then tested for their ability to inhibit *Candida albicans* TFIIB-dependent transcription in an in vitro transcription system such as that described herein, and also may be tested for their ability to inhibit *Candida albicans* growth.

Other fusion or modified protein systems that are contemplated include, but are not limited to, glutathione-S-transferase, maltose binding protein, influenza virus hemaglutinin, FLAG™ and hexahistidine fusions to *Candida albicans* TBP or *Candida albicans* TFIIB which are prepared, expressed, and purified by published methods or biotinylated *Candida albicans* TBP or TFIIB which are prepared using reactive biotin precursors available commercially. The purified fusion or modified protein is immobilized on a microtiter plate containing the appropriate ligand for each fusion protein (e.g. glutathione, amylose, CA157 antibody, etc., respectively) and the assay is carried out and the results evaluated in essentially the same manner as described above.

EXAMPLE 8

Candidate Inhibitors

A "candidate inhibitor," as used herein, is any compound with a potential to inhibit *Candida albicans* TFIIB-mediated transcription initiation or complex formation. A candidate inhibitor is tested in a concentration range that depends upon the molecular weight of the molecule and the type of assay. For example, for inhibition of protein/protein or protein/DNA complex formation or transcription initiation, small molecules (as defined below) may be tested in a concentration range of 1 pg-100 ug/ml, preferably at about 100 pg-20 ug/ml; large molecules, e.g., peptides, may be tested in the range of 10 ng-100 ug/ml, preferably 100 ng-10 ug/ml.

Inhibitors of *Candida albicans* growth or viability may target the novel transcription factor described herein, TFIIB, or it may target a protein or nucleic acid that interacts with the novel transcription factor so as to prevent the natural biological interaction that occurs in vivo and leads to transcription initiation in Candida. Thus, an inhibitor identified as described herein will possess two properties: 1) at some concentration it will inhibit *Candida albicans* growth or viability; and 2) at the same concentration, it will not significantly affect the growth of mammalian, particularly human, cells.

Candidate inhibitors will include peptide and polypeptide inhibitors having an amino acid sequence based upon the novel TFIIB sequences described herein. For example, a fragment of TFIIB may act as a competitive inhibitor with respect to TFIIB binding to other proteins involved in Candida transcription, e.g., RNA polymerase II, TBP, or with respect to binding of the transcription complex to the DNA template. One such candidate fragment is a fragment of TFIIB containing a classic zinc finger motif (sequence). This fragment spans a 35 amino acid region defined by residues 22–46 of the TFIIB sequence.

Candidate inhibitor compounds from large libraries of synthetic or natural compounds can be screened. Numerous means are currently used for random and directed synthesis of saccharide, peptide, and nucleic acid based compounds. Synthetic compound libraries are commercially available from a number of companies including Maybridge Chemical Co. (Trevillet, Cornwall, UK), Comgenex (Princeton, N.J.), Brandon Associates (Merrimack, N.H.), and Microsource (New Milford, Conn.). A rare chemical library is available from Aldrich (Milwaukee, Wis.). Combinatorial libraries are available and can be prepared. Alternatively, libraries of natural compounds in the form of bacterial, fungal, plant and animal extracts are available from e.g. Pan Laboratories (Bothell, Wash.) or MycoSearch (N.C.), or are readily produceable. Additionally, natural and synthetically produced libraries and compounds are readily modified through conventional chemical, physical, and biochemical means.

Useful compounds may be found within numerous chemical classes, though typically they are organic compounds, and preferably small organic compounds. Small organic compounds have a molecular weight of more than 50 yet less than about 2,500 daltons, preferably less than about 750, more preferably less than about 350 daltons. Exemplary classes include heterocycles, peptides, saccharides, steroids, and the like. The compounds may be modified to enhance efficacy, stability, pharmaceutical compatibility, and the like. Structural identification of an agent may be used to identify, generate, or screen additional agents. For example, where peptide agents are identified, they may be modified in a variety of ways to enhance their stability, such as using an unnatural amino acid, such as a D-amino acid, particularly D-alanine, by functionalizing the amino or carboxylic terminus, e.g. for the amino group, acylation or alkylation, and for the carboxyl group, esterification or amidification, or the like. Other methods of stabilization may include encapsulation, for example, in liposomes, etc.

EXAMPLE 9

Measurement For Effective Inhibition

The amount of inhibition by a candidate inhibitor is quantified using the following formula, which describes reactions reconstituted with a radioactively labeled moiety:

$$\text{Percent Inhibition} = \frac{(CPM_{Positive\ Control} - CPM_{Sample})}{(CPM_{Positive\ Control})} \times 100$$

where $CPM_{Positive\ Control}$ is the average of the cpm in complexes or RNA molecules formed in reactions that lack the candidate inhibitor, and $CPM_{Sample}$ is the cpm in complexes formed in reactions containing the candidate inhibitor. Candidate inhibitors for which the percent inhibition is 50% are titrated into reactions containing either *Candida albicans* TFIIB or human TFIIB (expressed in and purified from *E. coli* using existing recombinant clones (Peterson et al., *Science* 248, 1625–1630, 1990; Kao et al., *Science* 248, 1646–1650, 1990; Hoffman, et al., *Nature* 346, 387–390, 1990, and assayed as described above) and their $IC_{50}$ with respect to human and *Candida albicans* TFIIB determined from graphs of compound concentration vs. % inhibition. The $IC_{50}$ is defined as the concentration that results in 50% inhibition. Candidate inhibitors for which the $IC_{50}$ against *Candida albicans* TFIIB-containing reactions is less than or equal to ⅕the $IC_{50}$ against human TFIIB-containing reactions are further tested for their ability to inhibit the growth of *Candida albicans* in culture as described below.

EXAMPLE 10

Measurement For Inhibition of *Candida albicans* Growth in Culture

Once an inhibitor is identified in one or more of the binding or transcription assays described herein, it may be desirable to determine the effect of the inhibitor on the growth and/or viability of *Candida albicans* in culture. A candidate inhibitor is tested for its ability to inhibit growth of *Candida albicans* cells in culture as follows. Methods for performing tests on growth inhibition in culture are well-known in the art. Once such procedure is based on the NCCLS M27P method (The National Committee for Clinical Laboratory Standards, Reference Method for Broth Dilution Antifungal Susceptibility Testing of Yeasts; proposed standard, 1992), as follows. Serial dilutions (two- or three-fold steps starting from a maximum concentration of 100–200 µg/ml) of candidate inhibitor are prepared using RPMI-1640 medium as diluent and an aliquot of 100 µl of each dilution is added to the wells of a 96-well polystyrene microtiter plate. Five *Candida albicans* colonies, picked from a Sabouraud Dextrose Agar plate inoculated 14–20 hr previously with the test *Candida albicans* strain (Catalog number 10231 from the American Type Culture Collection Yeast Catalog), are suspended with RAMI-1640 medium such that the density of cells is 10,000–30,000 cells/ml. 100 ul of the cell suspension is added to each of the wells of the 96-well microtiter plate containing diluted candidate inhibitor and medium control. Cultures are mixed by agitation and incubated at 35° C. for 48 hr without agitation, after which cell growth is monitored by visual inspection for the formation of turbidity and/or mycelial colonies. The minimum concentration of candidate inhibitor at which no cell growth is detected by this method is defined as the minimum inhibitory concentration (MIC) for that compound. Examples of MICs for known antifungal compounds obtained using this technique are 0.125–0.5 µg/ml for fluconazole and 0.25–1.0 µg/ml for amphotericin B (The National Committee for Clinical Laboratory Standards, Reference Method for Broth Dilution Antifungal Susceptibility Testing of Yeasts; proposed standard, 1992). An inhibitor identified by the methods described herein, will have MIC which is equivalent to or less than the MICs for fluconazole or amphotericin B.

EXAMPLE 11

Transcription Inhibition Counterscreen Using Human TFIIB

A compound identified as an inhibitor of *Candida albicans* according to one or more of the assays described herein may be tested further in order to determine its effect on the host organism. In the development of useful antifungal compounds for human therapeutics, it is desirable that such compounds act as effective agents in inhibiting the viability of the fungal pathogen while not significantly inhibiting human cell systems. Specifically, inhibitors of *Candida albicans* identified in any one of the above described assays may be counterscreened for inhibition of human TFIIB.

Recombinant human TFIIB can be obtained from existing sources and purified by published methods (for example, see Peterson et al., Kao et al., and Hoffinan et al., supra) and contacted with the candidate inhibitor in assays such as those described above using a human system. The effectiveness of a *Candida albicans* TFIIB inhibitor as a human therapeutic is determined as one which exhibits a low level of inhibition against human TFIIB relative to the level of inhibition with respect to *Candida albicans* TFIIB. For example, it is preferred that the amount of inhibition by a given inhibitor of human TFllB in a human system be no more than 20% with respect to the amount of inhibition of *Candida albicans* TFIB in a Candida system when tested in any of the assays described above.

Dosage and Pharmaceutical Formulations

For therapeutic uses, inhibitors identified as described herein may be administered in a pharmaceutically acceptable/biologically compatible formulation, for example, in the form of a cream, ointment, lotion or spray for topical use, or in a physiological solution, such as a salt solution, for internal administration. The amount of inhibitor administered will be determined according to the degree of pathogenic infection and whether the infection is systemic or localized, and will typically be in the range of about 1 ug-100 mg/kg body weight. Where the inhibitor is a peptide or polypeptide, it will be administered in the range of about 100–500 ug/ml per dose. A single dose of inhibitor or multiple doses, daily, weekly, or intermittently, is contemplated according to the invention.

The route of administration will be chosen by the physician, and may be topical, oral, transdermal, nasal, rectal, intravenous, intramuscular, or subcutaneous.

Budapest Treatys Deposit

*E. coli* transformed with a plasmid containing the gene encoding *Candida albicans* TBP has been deposited in an international depository, the A.T.C.C., Rockville, Md., under the accession number 69900, on Sep. 15, 1995. *E. coli* transformed with a plasmid containing the gene encoding *Candida albicans* TFIIB has been deposited in an international depository, the A.T.C.C., Rockville, Md., under the accession number 69899, on Sep. 15, 1995. A.T.C.C. Nos. 69900 and 69889 will be available to the public upon the grant of a patent which discloses the accession numbers in conjunction with the invention described herein. The deposits were made under the Budapest Treaty, will be available beyond the enforceable life of the patent for which the deposit is made, and will be maintained for a period of at least 30 years from the time of deposit and at least 5 years after the most recent request for the furnishing of a sample of the deposit is received by the A.T.C.C. It is to be understood that the availability of these deposits does not constitute a license to practice the subject invention in derogation of patent rights granted for the subject invention by governmental action.

OTHER EMBODIMENTS

The foregoing examples demonstrate experiments performed and contemplated by the present inventors in making and carrying out the invention. It is believed that these examples include a disclosure of techniques which serve to both apprise the art of the practice of the invention and to demonstrate its usefulness. It will be appreciated by those of skill in the art that the techniques and embodiments disclosed herein are preferred embodiments only that in general numerous equivalent methods and techniques may be employed to achieve the same result.

All of the references identified hereinabove, are hereby expressly incorporated herein by reference to the extent that they describe, set forth, provide a basis for or enable compositions and/or methods which may be important to the practice of one or more embodiments of the present inventions.

---

We claim:

1. An isolated recombinant polypeptide comprising *Candida albicans* TFIIB.

2. An isolated fragment of *Candida albicans* TFIIB, said fragment being characterized in that it inhibits the biological activity of *Candida albicans* TFIIB in transcription initiation, wherein said fragment acts as a competitive inhibitor with respect to TFIIB binding to proteins involved in transcription.

3. An isolated fragment of *Candida albicans* TFIIB, said fragment being characterized in that it prevents the growth of *Candida albicans* upon contact with a *Candida albicans* culture.

4. A screening method for identifying an inhibitor of *Candida albicans* growth, comprising detecting inhibition of mRNA transcription in an in vitro transcription assay comprising a DNA template, RNA polymerase II, recombinant *Candida albicans* TFIIB, and a candidate inhibitor, wherein detection of said inhibition identifies said inhibitor of *Candida albicans* growth.

5. A screening method for identifying an inhibitor of *Candida albicans* growth, comprising detecting in the presence of a candidate inhibitor inhibition of formation of a complex comprising a DNA template and recombinant *Candida albicans* TFIIB, wherein inhibition of formation of said complex identifies said inhibitor of *Candida albicans* growth.

6. A screening method for identifying an inhibitor of *Candida albicans* growth, comprising detecting in the presence of a candidate inhibitor inhibition of formation of a complex comprising *Candida albicans* TFIIB and *Candida albicans* TBP, wherein inhibition of formation of said complex identifies said inhibitor of *Candida albicans* growth.

7. A screening method for identifying an inhibitor of *Candida albicans* growth, comprising detecting in the presence of a candidate inhibitor inhibition of formation of a complex comprising RNA polymerase II, *Candida albicans* TBP, and *Candida albicans* TFIIB, wherein inhibition of formation of said complex identifies said inhibitor of *Candida albicans* growth.

8. The screening method of claim 4, 5, 6 or 7, wherein said detecting is performed in the presence of a plurality of candidate inhibitors such that said inhibition is indicative of inhibition by one of said plurality of candidate inhibitors.

9. The screening method of claim 4, 5, 6 or 7, wherein a plurality of candidate inhibitors are screened, and wherein detection of inhibition by any one candidate inhibitor is detectable independently of said plurality.

* * * * *

SEQUENCE LISTING

```
(1) GENERAL INFORMATION:

(iii) NUMBER OF SEQUENCES: 4

(2) INFORMATION FOR SEQ ID NO: 1:

(i) SEQUENCE CHARACTERISTICS:
        (A) LENGTH: 660 base pairs
        (B) TYPE: nucleic acid
        (C) STRANDEDNESS: single
        (D) TOPOLOGY: linear (ii) MOLECULE TYPE: genomic DNA (xi) SEQUENCE DESCRIPTION: SEQ ID NO: 1:

ATG AAG TCA ATA GAG GAA GAT GAA AAA AAT AAA GCC GAA GAT TTG           45

GAT ATT ATA AAA AAG GAA GAC ATT GAT GAA CCT AAA CAA GAA GAT           90
```

-continued

```
ACC ACT GAT AGT AAT GGT GGT GGA GGT ATT GGT ATA GTG CCC ACA                 135

TTA CAA AAT ATT GTT GCT ACG GTG AAT CTT GAT TGT CGA CTT GAT                 180

CTT AAA ACA ATT GCT TTA CAT GCT AGA AAT GCC GAA TAT AAT CCA                 225

AAA CGT TTT GCT GCG GTG ATT ATG AGA ATT AGA GAT CCA AAA ACT                 270

ACG GCA TTA ATC TTT GCT TCG GGG AAA ATG GTT GTG ACT GGG GCT                 315

AAA TCC GAA GAT GAT TCC AAG TTG GCT TCA AGA AAG TAT GCT AGA                 360

ATC ATT CAA AAG TTG GGG TTC AAT GCT AAA TTT TGT GAT TTT AAA                 405

ATT CAA AAT ATA GTG GGG TCA ACA GAT GTT AAG TTT GCT ATT AGA                 450

TTA GAA GGC TTA GCT TTT GCT CAT GGT ACT TTC TCT TCA TAT GAA                 495

CCA GAA TTA TTT CCT GGG TTA ATT TAT AGA ATG GTG AAA CCA AAA                 540

ATT GTT TTA CTT ATA TTT GTT TCT GGG AAA ATT GTT TTG ACG GGT                 585

GCC AAA AAG AGA GAA GAA ATT TAT GAT GCA TTT GAA CTG ATT TAT                 630

CCG GTT TTA AAT GAA TTT CGT AAA AAT TGA                                     660
```

(2) INFORMATION FOR SEQ ID NO: 2:

(i) SEQUENCE CHARACTERISTICS:
        (A) LENGTH: 219 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Lys Ser Ile Glu Glu Asp Glu Lys Asn Lys Ala Glu Asp Leu
1               5                   10                  15

Asp Ile Ile Lys Lys Glu Asp Ile Asp Glu Pro Lys Gln Glu Asp
                20                  25                  30

Thr Thr Asp Ser Asn Gly Gly Gly Gly Ile Gly Ile Val Pro Thr
                35                  40                  45

Leu Gln Asn Ile Val Ala Thr Val Asn Leu Asp Cys Arg Leu Asp
                50                  55                  60

Leu Lys Thr Ile Ala Leu His Ala Arg Asn Ala Glu Tyr Asn Pro
                65                  70                  75

Lys Arg Phe Ala Ala Val Ile Met Arg Ile Arg Asp Pro Lys Thr
                80                  85                  90

Thr Ala Leu Ile Phe Ala Ser Gly Lys Met Val Val Thr Gly Ala
                95                  100                 105

Lys Ser Glu Asp Asp Ser Lys Leu Ala Ser Arg Lys Tyr Ala Arg
                110                 115                 120

Ile Ile Gln Lys Leu Gly Phe Asn Ala Lys Phe Cys Asp Phe Lys
                125                 130                 135

Ile Gln Asn Ile Val Gly Ser Thr Asp Val Lys Phe Ala Ile Arg
                140                 145                 150

Leu Glu Gly Leu Ala Phe Ala His Gly Thr Phe Ser Ser Tyr Glu
                155                 160                 165

Pro Glu Leu Phe Pro Gly Leu Ile Tyr Arg Met Val Lys Pro Lys
                170                 175                 180

Ile Val Leu Leu Ile Phe Val Ser Gly Lys Ile Val Leu Thr Gly
                185                 190                 195

Ala Lys Lys Arg Glu Glu Ile Tyr Asp Ala Phe Glu Ser Ile Tyr
                200                 205                 210
```

Pro Val Leu Asn Glu Phe Arg Lys Asn
                215             219

(2) INFORMATION FOR SEQ ID NO: 3:

(i) SEQUENCE CHARACTERISTICS:
        (A) LENGTH: 1095 base pairs
        (B) TYPE: nucleic acid
        (C) STRANDEDNESS: single
        (D) TOPOLOGY: linear (ii) MOLECULE TYPE: genomic DNA (xi) SEQUENCE DESCRIPTION: SEQ ID NO: 3:

| | |
|---|---:|
| TAAGCTTGTA TTACTAAGCA TATT ATG TCG CCA TCA ACA TCT ACG GCA | 48 |
| GTA CAG GAG TAT ATT GGA CCA AAC TTG AAT GTT ACA TTA ACA TGT | 93 |
| CCT GAG TGT AAG ATA TTT CCA CCT GAT TTG GTA GAG AGG TTC AGC | 138 |
| GAA GGT GAC ATT GTC TGT GGC AGT TGT GGG CTA GTA TTG AGT GAT | 183 |
| CGT GTT GTG GAT ACG AGA TCA GAA TGG AGA ACT TTC AGT AAC GAT | 228 |
| GAC CAA AAT GGT GAT GAT CCT TCT CGT GTT GGT GAT GCA GGT AAC | 273 |
| CCT TTA TTA GAC ACA GAG GAC TTG TCC ACA ATG ATT TCT TAT GCT | 318 |
| CCT GAT AGT ACC AAA GCA GGA AGA GAG TTA AGC CGA GCC CAA TCT | 363 |
| AAA TCT CTA GTC GAT AAA AAA GAC AAT GCA TTG GCT GCA GCA TAT | 408 |
| ATC AAG ATT TCT CAA ATG TGC GAT GGT TAT CAA TTG CCT AAA ATA | 453 |
| GTT CTG GAT GGG GCC AAG GAA GTC TAC AAA ATG GTT TAT GAC GAG | 498 |
| AAA CCA TTG CGA GGA AAA TCA CAA GAG AGT ATC ATG GCA GCT TCT | 543 |
| ATC TTT ATT GGT TGC AGA AAG GCC AAT GTT GCT CGT TCA TTC AAA | 588 |
| GAG ATA TGG GCA AAG ACT AAT GTA CCT CGT AAG GAA ATT GGT AAA | 633 |
| GTG TTC AAG ATC ATG GAC AAG ATC ATT CGT GAA AAG AAT GCA GCC | 678 |
| AAC CCT AAT GCT GCA TAT TAC GGT CAA GAC AGC ATT CAA ACC ACC | 723 |
| CAA ACT TCG GCC GAG GAT TTG ATT AGA AGA TTC TGT TCT CAC TTG | 768 |
| GGT GTT AAC ACA CAA GTT ACA AAT GGT GCG GAA TAC ATA GCC AGA | 813 |
| AGA TGT AAG GAA GTC GGG GTT TTA GCA GGT AGA TCG CCA ACT ACA | 858 |
| ATT GCT GCA ACT GTA ATT TAC ATG GCT TCA CTA GTG TTT GGA TTT | 903 |
| GAC TTA CCT CCA TCC AAG ATA TCT GAT AAA ACT GGT GTC AGT GAT | 948 |
| GGT ACT ATC AAA ACT TCA TAC AAG TAC ATG TAC GAG GAG AAA GAA | 993 |
| CAA TTG ATT GAT CCA TCT TGG ATA GAA AGT GGT AAA GTA AAA TTG | 1038 |
| GAA AAA ATA CCA AAA AAC TAA TACAGCGGAG TCGCCACTGT | 1079 |
| TAATCCTTTA CCCTCT | 1095 |

(2) INFORMATION FOR SEQ ID NO: 4:

(i) SEQUENCE CHARACTERISTICS:
        (A) LENGTH: 344 amino acids
        (B) TYPE: amino acid
        (D) TOPOLOGY: linear (ii) MOLECULE TYPE: protein (xi) SEQUENCE DESCRIPTION: SEQ ID NO: 4:

-continued

```
Met Ser Pro Ser Thr Ser Thr Ala Val Gln Glu Tyr Ile Gly Pro
1               5                   10                  15

Asn Leu Asn Val Thr Leu Thr Cys Pro Glu Cys Lys Ile Phe Pro
                20                  25                  30

Pro Asp Leu Val Glu Arg Phe Ser Glu Gly Asp Ile Val Cys Gly
                35                  40                  45

Ser Cys Gly Leu Val Leu Ser Asp Arg Val Val Asp Thr Arg Ser
                50                  55                  60

Glu Trp Arg Thr Phe Ser Asn Asp Asp Gln Asn Gly Asp Asp Pro
                65                  70                  75

Ser Arg Val Gly Asp Ala Gly Asn Pro Leu Leu Asp Thr Glu Asp
                80                  85                  90

Leu Ser Thr Met Ile Ser Tyr Ala Pro Asp Ser Thr Lys Ala Gly
                95                  100                 105

Arg Glu Leu Ser Arg Ala Gln Ser Lys Ser Leu Val Asp Lys Lys
                110                 115                 120

Asp Asn Ala Leu Ala Ala Tyr Ile Lys Ile Ser Gln Met Cys
                125                 130                 135

Asp Gly Tyr Gln Leu Pro Lys Ile Val Ser Asp Gly Ala Lys Glu
                140                 145                 150

Val Tyr Lys Met Val Tyr Asp Glu Lys Pro Leu Arg Gly Lys Ser
                155                 160                 165

Gln Glu Ser Ile Met Ala Ala Ser Ile Phe Ile Gly Cys Arg Lys
                170                 175                 180

Ala Asn Val Ala Arg Ser Phe Lys Glu Ile Trp Ala Lys Thr Asn
                185                 190                 195

Val Pro Arg Lys Glu Ile Gly Lys Val Phe Lys Ile Met Asp Lys
                200                 205                 210

Ile Ile Arg Glu Lys Asn Ala Ala Asn Pro Asn Ala Ala Tyr Tyr
                215                 220                 225

Gly Gln Asp Ser Ile Gln Thr Thr Gln Thr Ser Ala Glu Asp Leu
                230                 235                 240

Ile Arg Arg Phe Cys Ser His Leu Gly Val Asn Thr Gln Val Thr
                245                 250                 255

Asn Gly Ala Glu Tyr Ile Ala Arg Arg Cys Lys Glu Val Gly Val
                260                 265                 270

Leu Ala Gly Arg Ser Pro Thr Thr Ile Ala Ala Thr Val Ile Tyr
                275                 280                 285

Met Ala Ser Leu Val Phe Gly Phe Asp Leu Pro Pro Ser Lys Ile
                290                 295                 300

Ser Asp Lys Thr Gly Val Ser Asp Gly Thr Ile Lys Thr Ser Tyr
                305                 310                 315

Lys Tyr Met Tyr Glu Glu Lys Glu Gln Leu Ile Asp Pro Ser Trp
                320                 325                 230

Ile Glu Ser Gly Lys Val Lys Leu Glu Lys Ile Pro Lys Asn
                335                 340                 344
```